(12) United States Patent
Beausoleil

(10) Patent No.: US 7,228,016 B2
(45) Date of Patent: Jun. 5, 2007

(54) EVANESCENT NANOSENSOR USING AN OPTICAL RESONATOR

(75) Inventor: Raymond G. Beausoleil, Redmond, WA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 43 days.

(21) Appl. No.: 11/127,869

(22) Filed: May 11, 2005

(65) Prior Publication Data

US 2007/0036479 A1 Feb. 15, 2007

(51) Int. Cl.
*G02B 6/26* (2006.01)
(52) U.S. Cl. .......................................... 385/12; 385/30
(58) Field of Classification Search ................... 385/12, 385/30
See application file for complete search history.

(56) References Cited

U.S. PATENT DOCUMENTS

2006/0147169 A1* 7/2006 Sugita et al.

OTHER PUBLICATIONS

Akahane et al., "Fine-Tuned High-Q Photonic-Crystal Nanocavity," Optics Express, vol. 13, No. 4, pp. 1202-1214 (2005).
Warmuth et al., "Recent Highlights in Hemicarcerand Chemistry," Accounts of Chemical Research, vol. 34, No. 2, pp. 95-105 (2001).
Leontiev et al., "Encapsulation of Gases in the Solid State," Chem. Commun., 2004, pp. 1468-1469. (2004).

* cited by examiner

*Primary Examiner*—Tina M. Wong

(57) ABSTRACT

A sensor includes an optical resonator, a trap, and a measurement system. The trap is positioned to hold captured contaminant within an evanescent field of the optical resonator. The measurement system can detect the effect of the captured contaminant on the optical resonator. The sensor can includes a photonic crystal that contains defects forming the optical resonator and a waveguide to which the optical resonator is coupled. Yet another embodiment is a sensing method that exposes a trap that is adjacent to an optical resonator to an environment that may contain a contaminant that the trap can capture. Light having a wavelength that interacts with the contaminant can then be coupled into the optical resonator, and the effect of any captured contaminant on the optical resonator can be measured.

13 Claims, 3 Drawing Sheets

EVANESCENT NANOSENSOR USING AN
OPTICAL RESONATOR

CROSS-REFERENCE TO RELATED APPLICATION

This patent document is related to co-filed U.S. patent application Ser. No. 11/127,542, entitled "AUTONOMOUS EVANESCENT OPTICAL NANOSENSOR", which is hereby incorporated by reference in its entirety.

BACKGROUND

Detection of contaminants such as pollutants, toxins, poisons, and biological agents is critically important in many industrial, public, and private environments. Accordingly, a variety of environmental sensors have been developed. These environmental sensors are generally large enough to be handheld or mounted in the areas being monitored. Unfortunately, the size and need for separate mechanical and electrical components make these environmental sensors expensive when compared to the costs of integrated circuits. Sensors that could be manufactured using nanotechnology could potentially reduce sensing costs and permit new sensing capabilities, for example, for environments that are difficult to access or that have insufficient space to accommodate conventional sensors.

One group of sensors known in biomedical applications is the fiber-optic evanescent fluorescence sensors. These sensors generally sense or measure the concentrations of target molecules that are known to absorb light having a first wavelength $\lambda$ and to subsequently fluoresce by emitting light having a second wavelength $\lambda'$. Such sensors typical include an optical fiber that is inserted into a liquid containing the target molecules, while light having wavelength $\lambda$ is directed through the optical fiber. The target molecules that are within the evanescent field surrounding the optical fiber can then absorb light of wavelength $\lambda$ from the optical fiber and subsequently fluoresce to emit back into the optical fiber light having wavelength $\lambda'$. A detector coupled to the optical fiber measures the intensity of the light having frequency $\lambda'$, and that measurement indicates the presence or number of target molecules within the evanescent field of the optical fiber.

Current evanescent fluorescence sensors have a number of drawbacks. In particular, such sensors are relatively large and limited to sensing target molecules that have suitable fluorescent properties. Further, evanescent fluorescence sensors are typically limited to sensing target molecules in a liquid because molecules in a gas at room temperature spend only a short time within the evanescent field, i.e., within a distance of about $\lambda/4$ of the optical fiber, and therefore generally move away from the optical fiber before fluorescing.

In view of the limitations of current environmental sensors, inexpensive sensors and sensing methods for detecting a variety of contaminant species in a gas or a liquid are needed.

SUMMARY

In accordance with an aspect of the invention, a sensor includes an optical resonator, a trap, and a measurement system. The trap is positioned to hold a captured particle of a contaminant within an evanescent field of the optical resonator. The measurement system can detect the effect of the captured particles on the optical resonator.

In accordance with another embodiment of the invention, a sensor includes a photonic crystal. The photonic crystal contains defects that form a waveguide and an optical resonator coupled to the waveguide, and a trap is positioned to hold captured contaminant within an evanescent field of the optical resonator.

Yet another embodiment of the invention is a method for sensing contaminants. The method begins by exposing a trap that is adjacent to an optical resonator to an environment that may contain a contaminant that the trap can capture. Light having a wavelength that interacts with the contaminant can then be coupled into the optical resonator light, and the effect of any captured contaminant on the optical resonator can be measured.

BRIEF DESCRIPTION OF THE DRAWINGS

Use of the same reference symbols in different figures indicates similar or identical items.

DETAILED DESCRIPTION

In accordance with an aspect of the invention, a sensor can include contaminant traps on a passive optical resonator. Contaminants that the traps capture and hold in the evanescent field of the resonator change a property of the resonator such as the quality factor Q, the finesse F, or the photon lifetime $\tau$ in the resonator, so that measurements of the changed property can be used to detect the presence of a contaminant and to determine the concentration of the contaminant.

In accordance with a further aspect of the invention, a nanosensor fabricated in a photonic crystal or a photonic bandgap material includes an optical resonator with associated contaminant traps and further includes waveguides and photodiodes for measurement of a property such as the quality factor Q, the finesse F, or the photon lifetime $\tau$ for the resonator. In particular, defects in a photonic crystal can form the resonator, a first waveguide that receives an input optical signal, and a second waveguide into which the resonator couples the optical signal. Detectors in the nanosensor can measure the optical signals on one or both of the waveguides and determine the properties of the resonator. Current fabrication techniques for photonic crystals can produce a nanosensor having total area smaller than several square microns for use in airborne sensing applications.

Figure 1:
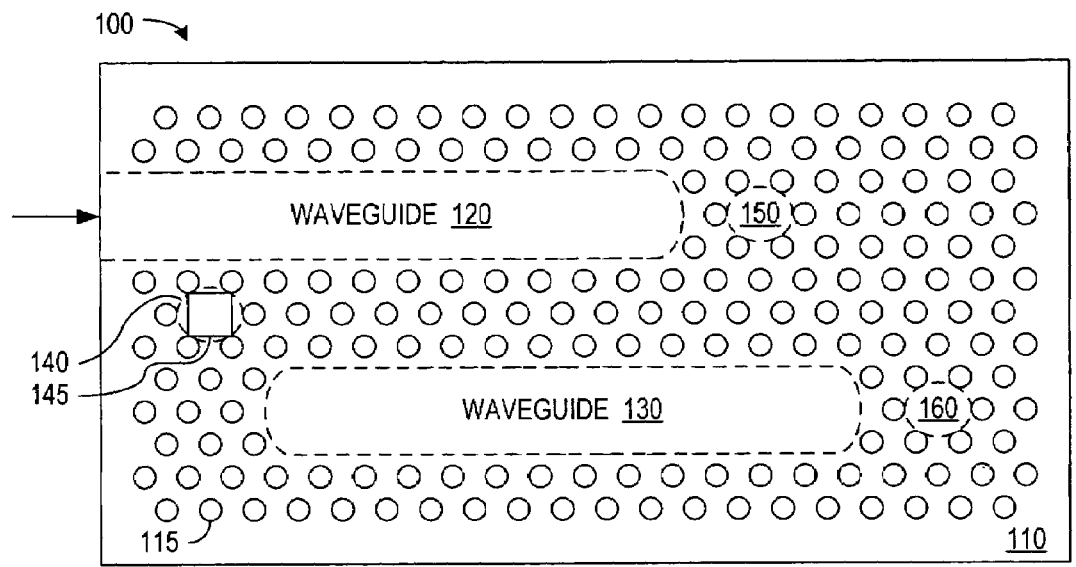
FIG. 1 shows a sensor in accordance with an embodiment of the invention having a contaminant trap on a resonator that is between line defects in a photonic crystal.

FIG. 1 illustrates an exemplary embodiment of a nanosensor 100 fabricated in and on a die 110. Die 110 may be a chip of a semiconductor material such as silicon or galliumarsenide (GaAs) that is processed to create a photonic crystal. Alternatively, die 110 can be a chip of a dielectric material such as silica or lithium niobate with overlying or underlying device layers for electrical elements as described further below. In general, at least a portion of die 110 through which an optical signal propagates is transparent to light having the wavelength λ of the optical signal. However, die 110 includes a periodic variation in its dielectric constant that creates a photonic bandgap material and prevents light with wavelengths λ from propagating in die 110 except in defect areas.

Many fabrication techniques for 2-D and 3-D photonic crystals have been developed or proposed and could be employed in embodiments of the present invention. However, in the illustrated embodiment of FIG. 1, die 110 is a 2-D photonic crystal formed with regions 115 having a dielectric constant that differs from the dielectric constant of the surrounding material. In a typical embodiment, regions 115 correspond to holes or air gaps since the dielectric constant of the air in a hole generally differs significantly from the dielectric constant of a solid material such as silicon. The spacing and size of regions 115 generally depend on the desired wavelength bandgap (or the optical signal wavelength λ) and the type of lattice for the arrangement of regions 115. However, for light having a wavelength λ of about 1.5 microns, the center-to-center spacing of regions 115 would typically be about 600 to 700 nm, with the diameters of regions 115 typically being about 400 to 500 nm. In such cases, regions 115 can be formed in die 110 using conventional photolithographic and etching techniques to form holes in die 110.

The pattern of regions 115 in die 110 includes defect areas that correspond to waveguides 120 and 130, a channel-drop filter 140, and detectors 150 and 160. Such defect areas can be areas in which regions 115 are absent or otherwise differ in size, spacing, or electrical properties from the periodically spaced regions 115 in the remaining area of die 110. Each of waveguides 120 and 130 can be a line defect or a series of resonators that act as a waveguide for an optical signal having wavelength λ. Channel drop filter 140 generally includes one or more resonators for light of wavelength λ. In operation, the optical signal is input to waveguide 120 and propagates along waveguide 120 to channel-drop filter 140, which transfers light from waveguide 120 to waveguide 130. Alternatively, waveguide 130 could be eliminated, and channel-drop filter 140 could couple light from waveguide 120 directly into detector 160. Detectors 150 and 160 are preferably photodiodes or other sensors that absorb and measure light that in the illustrated embodiment is from waveguides 120 and 130, respectively.

The relative intensity and shape of the optical signal that channel-drop filter 140 transfers from waveguide 120 to waveguide 130 generally depend on the characteristics of channel-drop filter 140. In accordance with an aspect of the invention, contaminant traps 145 can be applied to channel-drop filter 140 (or the entire surface of die 110), so that a set of traps 145 capture and hold contaminant particles in an evanescent field around channel-drop filter 140. The wavelength λ and the structure of traps 145 are preferably chosen so that an empty trap has little or no effect on the evanescent field of channel-drop filter 140, but a trap containing a particle of measured contaminant scatters light from channel-drop filter 140. As a result, properties of channel-drop filter 140 such as the quality factor Q, the finesse F, and the photon lifetime in channel-drop filter 140 depends on the number of contaminants in associated traps 145, and sensor 100 can determine the number of trapped contaminants present in traps 145 by measuring a property of channel-drop filter 140 that depends on the number of trapped contaminants.

Detectors 150 and 160, as in the illustrated embodiment of FIG. 1, can measure the optical signals from waveguides 120 and 130, respectively, for determination of a characteristic property (e.g., the quality factor Q) of the resonator 140. In an embodiment of the invention in which die 110 is made of a semiconductor material, detectors 150 and 160 can be photodiodes that are fabricated in defects that are resonators for the measured wavelength λ.

In an exemplary embodiment of the invention, when trap 145 is empty, channel-drop filter 140 has a high quality factor Q for light with the wavelength λ of the optical signal. A high-Q channel drop filter may be constructed in die 110 using one or more cavity resonators. For example, Akahane et al., "Fine-Tuned High-Q Photonic-Crystal Nanocavity," Optics Express, Vol. 13, No. 4, pp. 1202-1204, describes a design for a photonic-crystal nanocavity having a quality factor Q of up to 100,000 and is hereby incorporated by reference in its entirety. A high-Q channel-drop filter 140 can transfer nearly 100% of the light from waveguide 120 to waveguide 140, so that a zero (or near zero) measurement from detector 150 indicates a high-Q channel-drop filter with no contaminant in traps 145. Contaminant particles in traps 145 can scatter light back into waveguide 120, causing detector 150 to register a non-zero light intensity. In general, the amount of light detected will increase with each contaminant particle captured in traps 145. Accordingly, the presence of a contaminant can be detected from the measurement signal from detector 150.

An alternative measurement technique for measuring the quality factor Q or photon lifetime of channel-drop filter 140 uses a pulsed optical signal. In generally, a resonator will hold an optical signal for a characteristic decay time that depends on the photon lifetime or equivalently the quality factor Q of the resonator. Accordingly, circuit logic (not shown) can compare the measurement signal from detector 160 to the timing or waveform of an input optical pulse to waveguide 120 and determine the decay time of channel-drop filter 140. The quality factor Q of channel-drop filter 140 and the number of contaminant particles in traps 145 can be determined from the decay time.

Figure 2:
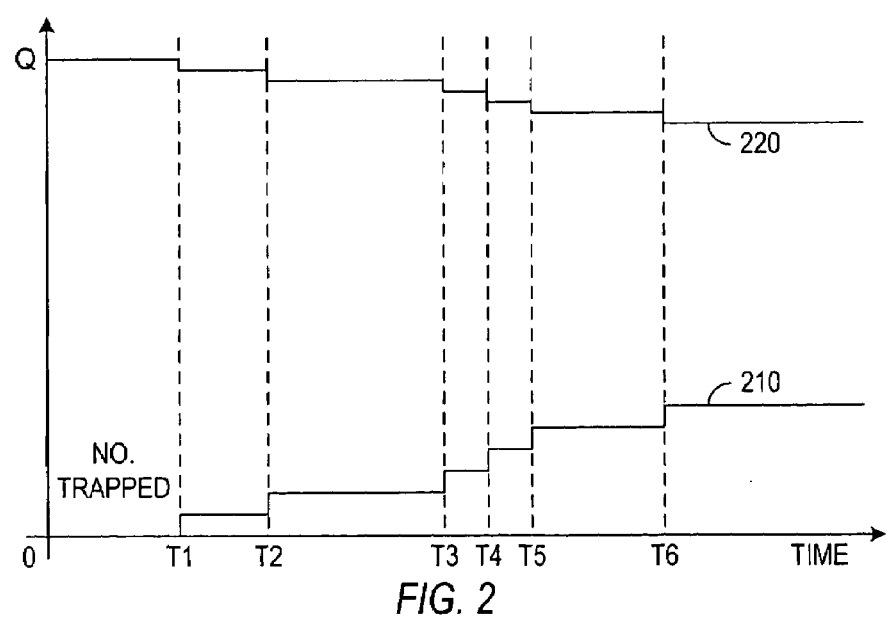
FIG. 2 shows plots illustrating the effect of captured contaminants on the quality factor Q of an optical resonator in a sensor in accordance with an embodiment of the invention.

FIG. 2 shows a plot 210 illustrating the time dependence of the number of particles of contaminant that traps 145 hold in the evanescent field of channel-drop filter 140. Ideally, traps 145 are protected from contaminants until a test start time (t=0) or are activated chemically or electromagnetically at the test start time. At a subsequent time T1, a first of the traps 145 captures a target contaminant, and the quality factor Q of channel-drop filter 140 falls. At subsequent times T2, T3, T4, T5, and T6, other traps 145 capture additional particles of the target contaminant.

FIG. 2 also shows a plot 220 illustrating the dependence of the quality factor Q of channel-drop filter 140 on the time or on the number of trapped particles of contaminant. Plot 220 of the quality factor Q is provided as an illustrative example of one specific property of an optical resonator that depends on the number of contaminant particles held in traps 145, but other properties of the resonator may demonstrate similar variations. As shown in FIG. 2, the quality factor Q of channel-drop filter 140 undergoes a discrete drop each time a trap 145 captures a particle of contaminant. The number of trapped particles of contaminant can be thus be inferred from the measurements of the quality factor Q. Further, the mean rate at which traps 145 capture contaminant particles increases with the concentration of the target contaminant in the surrounding environment. Accordingly, with appropriate calibration, analysis of the measurements to determine a time derivative or rate of change in the quality factor Q of channel-drop filter 140 will indicate the concentration of the target contaminant.

After sufficient exposure to contaminants, nearly all of the traps 145 will have captured a contaminant particle. Sensor 100 can then be discarded or cleaned.

Sensor 100 as described above uses traps 145 for capturing a target contaminant from a surrounding environment and for binding the captured contaminant within an evanescent field of an optical resonator. In different embodiments of the invention, each captured particle of the target contaminant may be, for example, an atom, a molecule, a virus, a microbe, or any trappable substance, and traps 145 generally have a chemistry or structure that is suitable and selected for capture of the target contaminant. Additionally, traps 145 must also firmly attach to the material of sensor 100, e.g., to silicon. Particular molecular groups such as chlorine derivatives of silane, are well known to bind strongly to silicon, silicon dioxide, and other materials. In an exemplary embodiment of the invention, die 110 is formed from silicon that is uniformly coated with a molecular group of chlorine derivatives of silane, which in turn irreversibly binds traps 145 to the surface of die 110, including over channel-drop filter 140.

Some atomic species of environmental contaminants that often need to be monitored include toxins such as arsenic (As) and lead (Pb), fissionable materials such as uranium (U) and plutonium (Pu), or other radioactive materials such as certain isotopes of strontium (Sr). A range of "host-guest" chemistries have been developed for capture of either a specific type of atom or an atom from a specific chemical family such as the alkali metals or the rare earth metals. These host-guest chemistries often discriminate among various atomic or ionic species based on the diameter of the atom or ion. Molecule cages known as carcerands or hemicarcerands, for example, can trap an atom (or a small molecule) and permanently hold the trapped contaminant. In an embodiment of the invention that measures or detects contaminant atoms or small molecules, traps 145 can be implemented as carcerands and/or hemicarcerands that create a cage of the size required to trap a particle of the target contaminant.

Another type of trap 130 for atomic contaminants uses a chelating compound, such as the well-known bidentate molecule ethylenediamine or the hexadentate molecule EDTA (ethylenediaminetetraacetate), which can form complexes with a target atom. Such chelates can also be bound to waveguide 120 using a chlorosilane chemistry such as mentioned above.

Chemistries that have been developed to complex many of the environmental pathogens or chemical agent molecules can also be used for traps 145 in sensor 100. For example, various bioactive pathogens attack particular molecular structures such as a protein or DNA in cells. For these pathogens, the specific protein or DNA strand may be used as "bait" trapping for the pathogen. Carcerands and other related systems have also been developed for capture of specific molecules (or a specific family of molecules) and could be used as traps 145 that bind a molecular species.

For a larger contaminant such as a virus, e.g. the polio or ebola virus, an antibody for the virus can be bound to die 110 as traps 145 because in many cases the antibody contains a protein that binds specifically to the external coating of the virus particle. Alternatively, a suitable protein from the antibody or any other type of molecule designed to recognize and bind to a particular virus could be used as traps 145, or a type of bait that resembles the lipid layer of a cell that attracts the virus could be used.

Finally, sensor 100 could successfully detect microbes using entities such as anthrax spores or other bacterial agents attached to channel-drop filter 140 as traps 145. Alternatively, the cell wall or coatings of microbe contaminants can be recognized or bound using specific proteins or sugars.

Figure 3:
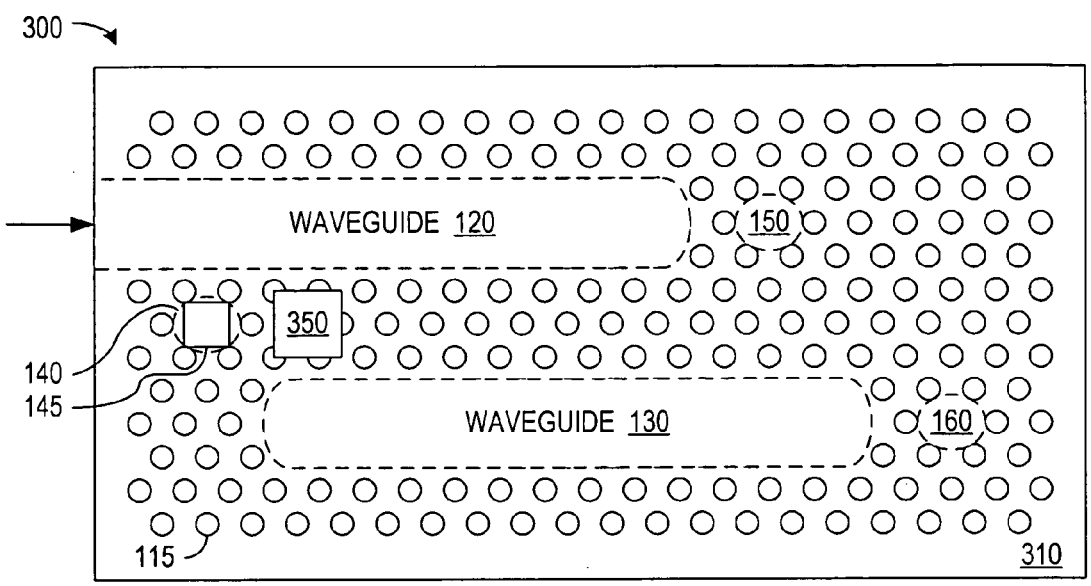
FIG. 3 shows a sensor in accordance with an embodiment of the invention that directly detects light scattered from an optical resonator.

FIG. 3 shows top view of a sensor 300 in accordance with an embodiment of the invention that does not require measurement of resonator properties to sense contaminants. Sensor 300 is fabricated on a die 310 that like die 110 of FIG. 1 is processed to create a photonic crystal having defects corresponding to waveguides 120 and 130, channel-drop filter 140, and detectors 150 and 160, as described above. Traps 145 as described above operate to capture and hold contaminant particles in the evanescent field of resonator 140. Sensor 300 additionally includes a detector 350 that is positioned to detect light that contaminants in traps 145 scatter out of channel-drop filter 140. Detector 350 may, for example, be a photodiode fabricated in a semiconductor region overlying die 310. A measurement signal indicating the intensity of light detected by detector 350 will directly depend on the number of contaminant particles scattering light, thus a determination of the quality factor Q or another property of channel-drop filter 140 is not required. Optionally, detector 150 and/or 160 could be omitted from sensor 300 or used in combination with detector 350, for example, to determine the intensity of the input optical signal or to determine the quality factor Q of channel-drop cavity 140 in addition to measurement of the scattered light.

Figure 4:
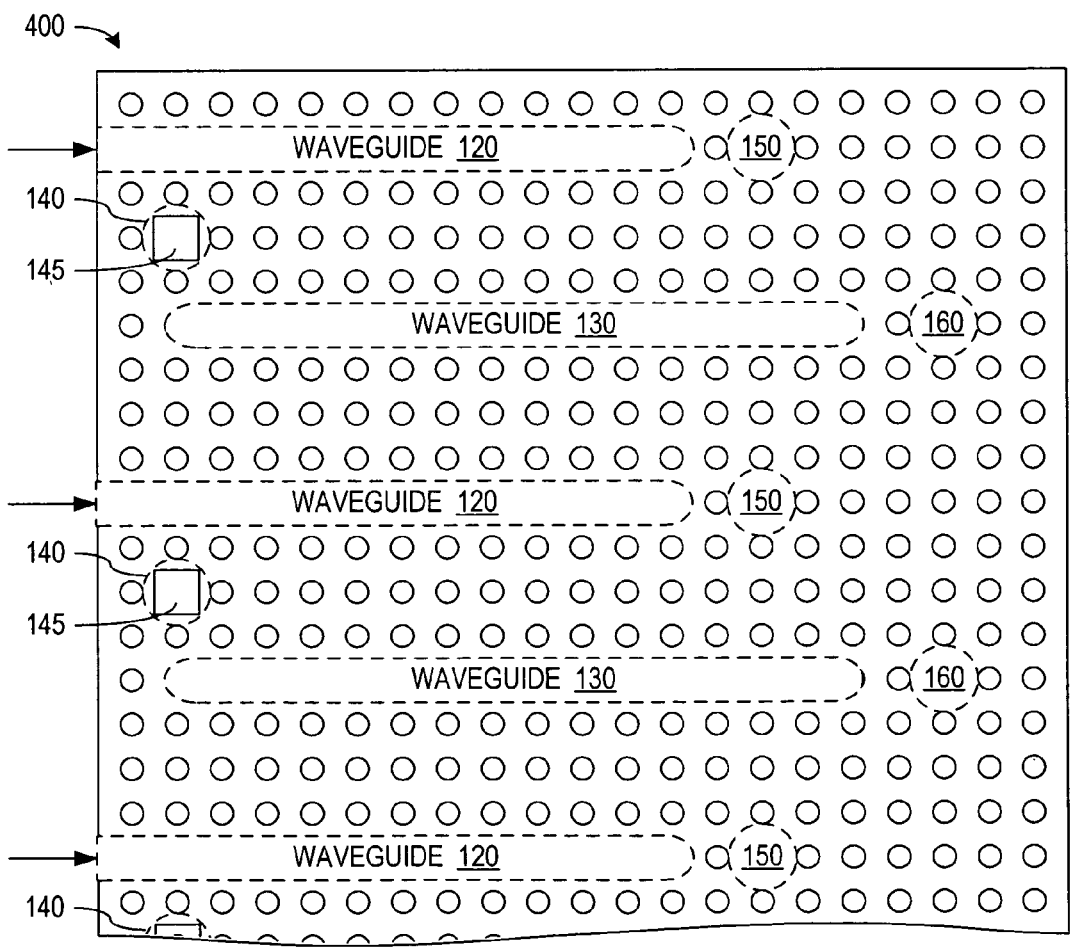
FIG. 4 shows a sensor in accordance with an embodiment of the invention employing multiple optical resonators with associated contaminant traps.

FIG. 4 shows a sensor 400 in accordance with an embodiment of the invention including multiple repetitions of the sensing structure of FIG. 1. In particular, sensor 400 includes multiple pairs of waveguides 120 and 130, with each pair having a corresponding channel-drop filter 140. Each of the channel-drop filters 140 can be coated with the same type of traps 145 or with different types of traps 145. When all of the traps 145 are the same, the measured characteristic of or the scattering from each channel-drop filter 140 can be independently determined to provide a combined measurement with better statistics and/or reliability. Alternatively, two or more of channel-drops 140 can be coated with different types of traps for the same contaminant. In such a configuration, independent measurements of the contaminants captured in the different types of traps can be compared to avoid a false detection of a particular contaminant or to distinguish among multiple contaminants that one or more of the different types of traps may capture.

Figure 5:
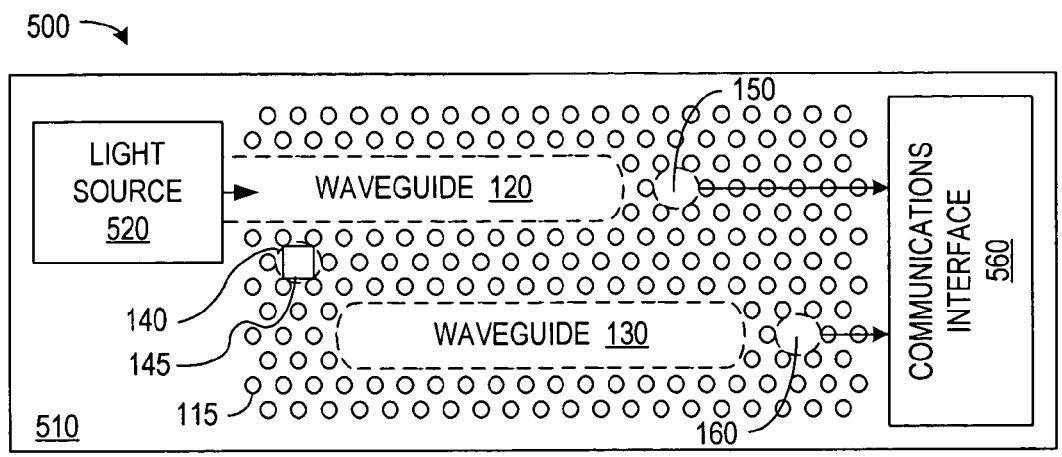
FIG. 5 illustrates an autonomous nanosensor in accordance with an embodiment of the invention.

In accordance with a further aspect of the invention, sensors such as those described above may be made small and autonomous. FIG. 5, for example, illustrates a nanosensor 500 in accordance with an embodiment of the invention in which a die 510 includes a light source 510 and a communications interface 560. Die 510 additionally includes a photonic crystal with defects for waveguides 120 and 130, channel-drop filter 140, and detectors 150 and 160 as described above. Light source 520 can be a laser diode or a light emitting diode that transmits an optical signal of the desired wavelength λ on waveguide 120. Communication interface 560 can be an RF transceiver with associated circuitry for processing and transmitting measurement data. Power for electronic elements may be provided by an on-chip device such as photovoltaic cell or from an electromagnetic signal received by communications interface 560.

Figure 6:
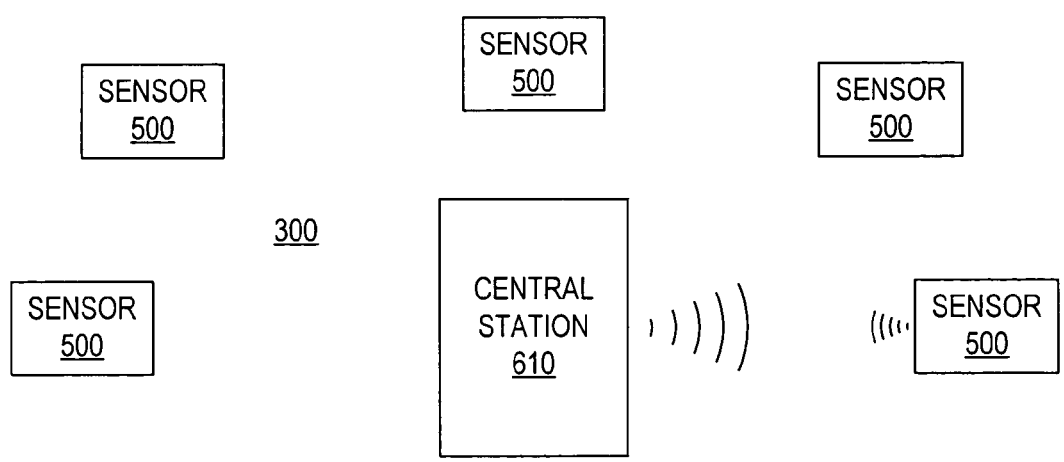
FIG. 6 illustrates a system in accordance with an embodiment of the invention employing autonomous sensors to detect the distribution of contaminants in an environment.

FIG. 6 illustrates a system 600 for using autonomous sensors 500 to measure the presence, concentration, and/or distribution of a target contaminant. For system 600, a collection of nanosensors 500 that are small enough to remain suspended in air, are released into an environment to be tested for one or more target contaminants. Nanosensors 500 may, for example, be released into a ventilation system in a building. Traps in each nanosensor 500 can then capture contaminant particles as nanosensors 500 move through the environment.

A central station 610 can be moved to any location where nanosensors 500 are present. In the illustrated embodiment, central station 610 includes a transmitter that transmits a signal to activate one or more nanosensors 500. The transmitted activation signal may, for example, be a radio or microwave signal that communications interfaces 560 receive and convert to power that operates light sources 520 and other circuit elements in sensors 500. If desired, the activation signal can be directional or of limited range so that only nanosensors 500 in a particular area are activated.

The activated nanosensors 500 transmit back measurement signals indicating the number of captured contaminants in the activated nanosensors 500. Central station 610 can continue monitoring or polling the measurement signals from nanosensors 500 over a period of time sufficient to determine a rate of increase of the measurement signals and from the rate of increase determine the concentration of the contaminant in the area of the activated nanosensors 500.

Although the invention has been described with reference to particular embodiments, the description is only an example of the invention's application and should not be taken as a limitation. For example, although the above embodiments describe use of optical signals, light, and light sources, it should be understood that embodiments of the invention are not limited to use of visible light but more generally can employ other wavelengths of electromagnetic radiation that provide an evanescent field suitable for detection of target contaminants. Various other adaptations and combinations of features of the embodiments disclosed are within the scope of the invention as defined by the following claims.

What is claimed is:

1. A sensor comprising:
    an optical resonator;
    a trap positioned to hold a captured particle of a contaminant within an evanescent field around the optical resonator; and
    a measurement system capable of detecting an effect of captured particles on the optical resonator, wherein the measurement system measures a change in a characteristic of the optical resonator, and the characteristic is selected from the group consisting of a quality factor, a finesse, and a photon lifetime of the optical resonator.

2. The sensor of claim 1, further comprising a first waveguide, wherein the optical resonator is coupled to extract light from the first waveguide.

3. The sensor of claim 2, further comprising a photonic crystal, wherein defects in the photonic crystal form the optical resonator and the first waveguide.

4. The sensor of claim 2, wherein the measurement system measures change in the quality factor Q of the optical resonator by measuring an intensity of light that propagates through the waveguide and past the optical resonator.

5. The sensor of claim 1, wherein the trap is one among a plurality of traps that are positioned to hold captured particles in the evanescent field around the optical resonator.

6. A sensor comprising:
    an optical resonator;
    a first waveguide, wherein the optical resonator is coupled to extract light from the first waveguide;
    a trap positioned to hold a captured particle of a contaminant within an evanescent field around the optical resonator; and
    a measurement system capable of detecting an effect of captured particles on the optical resonator, wherein the measurement system comprises:
    a second waveguide coupled to the optical resonator; and
    a detector positioned to measure an intensity of light that propagates through the second waveguide.

7. The sensor of claim 6, wherein the measurement system measures a decay time of an optical pulse coupled into the optical resonator.

8. A sensor comprising:
    an optical resonator;
    a trap positioned to hold a captured particle of a contaminant within an evanescent field around the optical resonator, wherein the trap comprises a carcerand; and
    a measurement system capable of detecting an effect of captured particles on the optical resonator.

9. A sensor comprising:
    a photonic crystal containing defects that form a waveguide and an optical resonator coupled to the waveguide;
    a trap positioned to hold a captured particle of a contaminant within an evanescent field of the optical resonator; and
    a detector fabricated within a defect in the photonic crystal.

10. The sensor of claim 9, wherein the defect containing the detector is positioned to measure an intensity of an optical signal that propagates through the waveguide past the optical resonator.

11. The sensor of claim 9, wherein the photonic crystal further comprises one or more defects that form a second waveguide.

12. The sensor of claim 11, wherein the detector is positioned to measure an intensity of an optical signal that propagates through the second waveguide.

13. A method for sensing contaminants, comprising:
    exposing a trap that is adjacent to an optical resonator to an environment that may contain a contaminant that the trap is capable of capturing;
    coupling into the optical resonator light having a wavelength that interacts with the contaminant;
    measuring light from the optical resonator to detect an effect of any captured contaminant on the optical resonator; and
    determining a change in a characteristic of the optical resonator, wherein the characteristic is selected from the group consisting of a quality factor, a finesse, and a photon lifetime of the optical resonator.

* * * * *